US010413037B2

(12) United States Patent
Yamanaka et al.

(10) Patent No.: US 10,413,037 B2
(45) Date of Patent: Sep. 17, 2019

(54) COSMETIC

(71) Applicant: TAIKI CORP., LTD., Osaka-shi, Osaka (JP)

(72) Inventors: Reiko Yamanaka, Osaka (JP); Yukiko Doi, Osaka (JP); Toshihiko Ohira, Osaka (JP)

(73) Assignee: TAIKI CORP., LTD., Osaka-shi (JP)

( * ) Notice: Subject to any disclaimer, the term of this patent is extended or adjusted under 35 U.S.C. 154(b) by 0 days.

(21) Appl. No.: 15/753,736

(22) PCT Filed: Aug. 16, 2016

(86) PCT No.: PCT/JP2016/073885
§ 371 (c)(1),
(2) Date: Feb. 20, 2018

(87) PCT Pub. No.: WO2017/033797
PCT Pub. Date: Mar. 2, 2017

(65) Prior Publication Data
US 2018/0235344 A1   Aug. 23, 2018

(30) Foreign Application Priority Data

Aug. 21, 2015  (JP) .................................. 2015-163434

(51) Int. Cl.
*A45D 34/04*  (2006.01)
*A61Q 1/02*   (2006.01)
(Continued)

(52) U.S. Cl.
CPC ........... *A45D 34/04* (2013.01); *A45D 33/005* (2013.01); *A45D 33/34* (2013.01); *A61K 8/02* (2013.01);
(Continued)

(58) Field of Classification Search
CPC .... A45D 33/005; A45D 33/006; A45D 33/34; A45D 2200/1036; A61K 8/02; A61Q 1/02; D04H 1/54; D04H 1/541
See application file for complete search history.

(56) References Cited

U.S. PATENT DOCUMENTS 9,422,652 B2 *   8/2016   Terada .................... D04H 1/541
2009/0318050 A1 * 12/2009  Okaya ....................... D01F 8/06
                                                                        442/359
(Continued)

FOREIGN PATENT DOCUMENTS

JP       10-113223 A      5/1998
JP       2005-177176 A    7/2005
(Continued)

OTHER PUBLICATIONS

International Search Report dated Oct. 11, 2016, issued in Counterpart of International Application No. PCT/JP2016/073885 (2 pages).

*Primary Examiner* — Nicholas J. Weiss
(74) *Attorney, Agent, or Firm* — Westerman, Hattori, Daniels & Adrian, LLP

(57) ABSTRACT

An elastic body for cosmetic holding use which can be used for holding a cosmetic such as a foundation, such as a puff that can be used for the application of a cosmetic onto skin, said elastic body being characterized by containing conjugate fibers as constituent fibers, wherein each of the conjugate fibers contains a resin A and a resin B having a higher melting temperature than that of the resin A, and contact parts between the constituent fibers are integrated with the resin A contained in the conjugate fibers; a cosmetic-containing elastic body which comprises the elastic body for cosmetic holding use and a cosmetic contained in the elastic body; and a cosmetic equipped with the cosmetic-containing elastic body.

8 Claims, 3 Drawing Sheets

(51) Int. Cl.
*A61K 8/02* (2006.01)
*D04H 1/541* (2012.01)
*A45D 33/00* (2006.01)
*A45D 33/34* (2006.01)

(52) U.S. Cl.
CPC ............... *A61Q 1/02* (2013.01); *D04H 1/541* (2013.01); *A45D 2200/1036* (2013.01); *D10B 2331/04* (2013.01); *D10B 2401/041* (2013.01); *D10B 2503/00* (2013.01)

(56) References Cited

U.S. PATENT DOCUMENTS

| | | |
|---|---|---|
| 2010/0261399 A1 | 10/2010 | Katsuya et al. |
| 2014/0023689 A1 | 1/2014 | Kim et al. |
| 2015/0079862 A1 | 3/2015 | Jeong et al. |
| 2015/0173975 A1* | 6/2015 | Harumoto ........... A61F 13/5116 604/370 |

FOREIGN PATENT DOCUMENTS

| | | |
|---|---|---|
| JP | 2011-506778 A | 3/2011 |
| JP | 5465357 B2 | 4/2014 |
| JP | 2015-513987 A | 5/2015 |

* cited by examiner ized by sunlight and the like. Accordingly, there is a
COSMETIC

TECHNICAL FIELD

The present invention relates to a cosmetic product. More specifically, the present invention relates an elastic body for holding a cosmetic, which is used for holding the cosmetic; a cosmetic-containing elastic body, which contains a cosmetic in the elastic body for holding the cosmetic; and a cosmetic product having the cosmetic-containing elastic body. The elastic body for holding a cosmetic according to the present invention can be suitably used in, for example, a puff which is used in applying a cosmetic to a skin and the like, and various cosmetic products such as a foundation.

BACKGROUND ART

A liquid cosmetic such as a foundation has been housed in a cosmetic container such as a compact. The cosmetic container has a container body and a lid, and an elastic body for holding a liquid cosmetic is housed in the container body. As the elastic body for holding a cosmetic, conventionally, a soft sponge such as a polyethylene foam or a polyurethane foam has been used. In recent years, as an elastic body for holding a cosmetic having a stable maintenance property of a cosmetic, a polyether urethane foam has been proposed (for example, see Patent Literature 1).

According to the polyether polyurethane foam, a liquid cosmetic existing on the surface of the foam can be easily adhered to a puff and the like. Since the foam has a cell structure, when a liquid cosmetic is incorporated into the foam, the liquid cosmetic is held in cells of the foam. Accordingly, the liquid cosmetic cannot be easily taken out to the outside of the foam by means of a puff and the like. The polyether polyurethane foam therefore has a disadvantage such that the liquid cosmetic which is not taken out from the foam remains in the foam in a large amount. Furthermore, since the polyurethane foam is not a fiber but a foam having a urethane bond, and has a large surface area as a whole, the foam is low in light fastness, and is apt to be yellowed by sunlight and the like. Accordingly, there is a possibility that the foam causes lowering in product value.

PRIOR ART LITERATURES

Patent Literatures

Patent Literature 1; Japanese Patent No. 5465357

SUMMARY OF THE INVENTION

Problems to be Solved by the Invention

The present invention has been made in view of the above-mentioned prior arts. An object of the present invention is to provide an elastic body for holding a cosmetic, from which a cosmetic which is incorporated into the elastic body can be efficiently taken out to the outside thereof; a cosmetic-containing elastic body which contains a cosmetic in the elastic body for holding a cosmetic; and a cosmetic product having the cosmetic-containing elastic body.

Means for Solving the Problems

The present invention relates to
(1) an elastic body for holding a cosmetic, which includes constituent fibers containing a conjugate fiber, wherein the conjugate fiber includes a resin A and a resin B of which melting temperature is higher than that of the resin A, and the contact part between the constituent fibers is integrated with the resin A of the conjugate fiber,
(2) a cosmetic-containing elastic body including a cosmetic in the elastic body according to the above item (1), and
(3) a cosmetic product including the cosmetic-containing elastic body according to the above item (2).

Effects of the Invention

The elastic body for holding a cosmetic of the present invention exhibits excellent effects that a cosmetic which is incorporated into the inside of the elastic body can be efficiently taken out to the outside of the elastic body. The cosmetic-containing elastic body of the present invention exhibits excellent effects that a cosmetic which is incorporated into the inside of the elastic body can be efficiently taken out to the outside of the elastic body, since the cosmetic is contained in the above-mentioned elastic body for holding a cosmetic. In addition, the cosmetic product of the present invention exhibit excellent effects that a cosmetic which is incorporated into the inside of the elastic body can be efficiently taken out to the outside of the elastic body, since the cosmetic product has the above-mentioned cosmetic-containing elastic body.

BRIEF DESCRIPTION OF THE DRAWINGS

FIG. 2 (b) is an optical microscope photograph substituted with a drawing, which shows a cross section of the sample A obtained in Example 1 in a thickness direction.

FIG. 3 (b) is an optical microscope photograph substituted with a drawing, which shows a result of a light fastness test of a sample B in Experimental example 1; FIG. 3 (c) is an optical microscope photograph substituted with a drawing, which shows a result of a light fastness test of a sample C in Experimental example 1; FIG. 3 (d) is an optical microscope photograph substituted with a drawing, which shows a result of a light fastness test of a sample R1 in Experimental example 1; and FIG. 3 (e) is an optical microscope photograph substituted with a drawing, which shows a result of a light fastness test of a sample R2 in Experimental example 1.

MODE FOR CARRYING OUT THE INVENTION

Figure 1A:
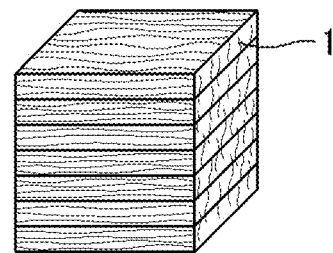
FIGS. 1(a)-1(d) are schematic explanatory drawings which shows one embodiment of a method for producing a web sheet which is used in producing the elastic body for holding a cosmetic of the present invention.
Figure 1B:
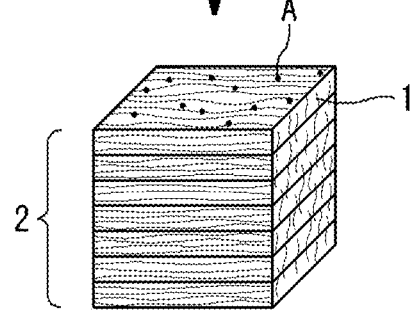
Figure 1C:
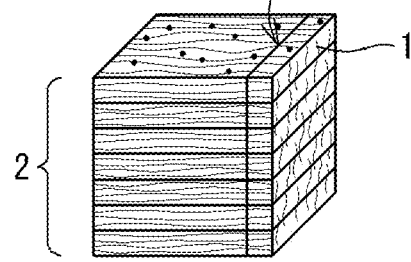
Figure 1D:
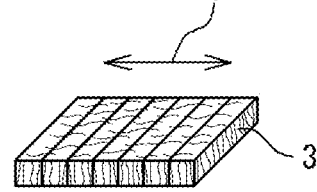

The elastic body for holding a cosmetic of the present invention is an elastic body for holding a cosmetic, which is used for holding a cosmetic as described above, and is characterized in that the elastic body includes constituent fibers containing a conjugate fiber, wherein the conjugate fiber includes a resin A and a resin B of which melting temperature is higher than that of the resin A, and the contact part between the constituent fibers is integrated with the resin A of the conjugate fiber.

The melting temperature of the resin A which constitutes the conjugate fiber is lower than the melting temperature of the resin B. The melting temperature of the resin A is preferably lower than the melting temperature of the resin B by 20° C. or more, and is more preferably lower than the melting temperature of the resin B by 30° C. or more, from the viewpoint of prevention of the conjugate fiber from permanent set in fatigue. The melting temperature of the resin A is preferably 130 to 220° C. from the viewpoint of prevention of the conjugate fiber from permanent set in fatigue, and firm integration of the contact part between the constituent fibers with the resin A.

Incidentally, when the melting temperature of the resin A and the melting temperature of the resin B, and the melting temperature of a synthetic fiber mentioned later cannot be distinctly determined, the melting temperature is replaced with its softening temperature.

The resin A includes, for example, a polyester, a thermoplastic elastomer and the like, and the present invention is not limited only to those exemplified ones.

The polyester includes, for example, polyethylene terephthalate, polytrimethylene terephthalate, polybutylene terephthalate, polyhexamethylene terephthalate, polytetramethylene terephthalate, poly1,4-dimethylcyclohexane terephthalate, polyhydrolactone and the like, and the present invention is not limited only to those exemplified ones. These polyesters can be used alone or at least two kinds thereof can be used in combination. Among these thermoplastic polyesters, polyethylene terephthalate, polytrimethylene terephthalate, polybutylene terephthalate and polyhexamethylene terephthalate are preferred, since these polyesters are excellent in light fastness.

The thermoplastic elastomer includes, for example, a polyester elastomer, a polyurethane elastomer and the like. Among these elastomers, the polyester elastomer is preferred from the viewpoint of improvement in light fastness of the elastic body for holding a cosmetic of the present invention.

The polyester elastomer includes, for example, a polyester elastomer such as polyethylene terephthalate elastomer, a polyether-ester block copolymer having a polyester segment as a hard segment and a poly (alkylene oxide) glycol segment as a soft segment. The polyether-ester block copolymer can be prepared, for example, by reacting a dicarboxylic acid, a diol and a poly(alkylene oxide) glycol.

The above-mentioned dicarboxylic acid includes, for example, aromatic dicarboxylic acids such as o-phthalic acid, m-phthalic acid, terephthalic acid, naphthalene-2,6-dicarboxylic acid, naphthalene-2,7-dicarboxylic acid, diphenyl-4,4'-dicarboxylic acid, diphenoxyethane dicarboxylic acid and sodium 3-sulfoisophthalate; alicyclic dicarboxylic acid such as 1,4-cyclohexanedicarboxylic acid; and aliphatic dicarboxylic acids such as succinic acid, oxalic acid, adipic acid, sebacic acid, dodecanedioic acid and dimer acid. The present invention is not limited only to those exemplified ones. These dicarboxylic acids can be used alone, or at least two kinds thereof can be used in combination.

The above-mentioned diol includes, for example, aliphatic diols such as ethylene glycol, trimethylene glycol, tetramethylene glycol, pentamethylene glycol, hexamethylene glycol, 1,4-butanediol, neopentyl glycol and decamethylene glycol; alicyclic diols such as 1,1-cyclohexanedimethanol, 1,4-cyclohexanedimethanol and tricyclodecanedimethanol; and the like. The present invention is not limited only to those exemplified ones. These diols can be used alone, or at least two kinds thereof can be used in combination.

The above-mentioned poly(alkylene oxide) glycol includes, for example, polyethylene glycol, poly(1,2-propylene oxide) glycol, poly(1,3-propylene oxide) glycol, poly (tetramethylene oxide) glycol, ethylene oxide-propylene oxide copolymer, ethylene oxide-tetrahydrofuran copolymer and the like, and the present invention is not limited only to those exemplified ones. These poly(alkylene oxide) glycols can be used alone, or at least two kinds thereof can be used in combination. It is preferred that the number average molecular weight of the poly(alkylene oxide) glycol is 400 to 5000 or so.

The intrinsic viscosity of the polyester elastomer is preferably 0.8 to 1.7, and more preferably 0.9 to 1.5, from the viewpoint of firm integration of the contact part between the constituent fibers with the resin A.

The polyurethane elastomer can be obtained by, for example, polymerizing a polyol with a diisocyanate in the presence of a chain extender.

The polyol includes, for example, polyols having a molecular weight of 500 to 6000 or so, such as dihydroxy polyether, dihydroxypolyester, dihydroxypolycarbonate and dihydroxypolyesteramide, and the present invention is not limited only to those exemplified ones. These polyols can be used alone, or at least two kinds thereof can be used in combination.

The diisocyanate includes, for example, diisocyanates having a molecular weight of 500 or less, such as diphenylmethane diisocyanate, tolylene diisocyanate, isophorone diisocyanate, hydrogenated diphenylmethane diisocyanate, xylylene diisocyanate, diisocyanate methylcaproate and hexamethylene diisocyanate, and the present invention is not limited only to those exemplified ones. These diisocyanates can be used alone, or at least two kinds thereof can be used in combination.

The chain extender includes, for example, ethylene glycol, amino alcohol, bishydroxyethoxybenzene, 1,4-butanediol and the like, and the present invention is not limited to only those exemplified ones. These chain extenders can be used alone, or at least two kinds thereof can be used in combination.

As the thermoplastic elastomer, a polyether polyester having a polybutylene terephthalate segment as a hard segment, and a polyoxybutylene glycol segment as a soft segment can be used from the viewpoint of firm integration of a contact part of the constituent fibers with the resin A.

In the above-mentioned hard segment, a part of an acid component which is used as a raw material of the polybutylene terephthalate can be replaced with an acid such as a dicarboxylic acid other than terephthalic acid, or an oxycarboxylic acid within a scope which would not hinder an object of the present invention. In addition, a part of butyl alcohol which is used as a raw material of the polyoxybutylene glycol can be replaced with other polyhydric alcohol within a scope which would not hinder an object of the present invention.

In the above-mentioned soft segment, a part of butylene glycol which is used as a raw material of the polyoxybutylene glycol can be replaced with other polyhydric alcohol within a scope which would not hinder an object of the present invention.

The resin B includes, for example, a thermoplastic polyester and the like, and the present invention is not limited only to the exemplified one.

The thermoplastic polyester includes, for example, polyethylene terephthalate, polytrimethylene terephthalate, polybutylene terephthalate, polyhexamethylene terephthalate, polytetramethylene terephthalate, poly1,4-dimethylcyclohexane terephthalate, polyhydrolactone and the like, and the present invention is not limited to only those exemplified ones. These thermoplastic polyesters can be used alone, or at least two kinds thereof can be used in combination. Among the thermoplastic polyesters, polyethylene terephthalate, polytrimethylene terephthalate, polybutylene terephthalate and polyhexamethylene terephthalate are preferred, since these polyesters are excellent in light fastness.

The melting temperature of the resin B is preferably higher than the melting temperature of the resin A by 20° C. or higher, and more preferably higher than the melting temperature of the resin A by 30° C. or higher, from the viewpoint of prevention of the conjugate fiber from permanent set in fatigue. The melting temperature of the resin B is preferably 150 to 270° C., and more preferably 160 to 270° C., from the viewpoint of prevention of the conjugate fiber from permanent set in fatigue, and firm integration of a contact part between the constituent fibers with the resin A.

In the conjugate fiber, it is preferred that the resin A is the polyester or the polyester elastomer, and that the resin B is the thermoplastic polyester, from the viewpoint of improvement in light fastness, prevention of the conjugate fiber from permanent set in fatigue, and firm integration of a contact part between the constituent fibers with the resin A.

It is preferred that 30 to 70% of the surface area of the conjugate fiber is composed of the resin A, and that 70 to 30% of the surface area of the conjugate fiber is composed of the resin B from the viewpoint of firm integration of a contact part between the constituent fibers with the resin A.

The conjugate fiber includes the resin A and the resin B having a melting temperature higher than that of the resin A, and a resin other than the resin A and the resin B can be included in the conjugate fiber within a scope which would not hinder an object of the present invention.

The conjugate fiber includes, for example, a core-sheath type conjugate fiber, a side-by-side type conjugate fiber, a sea-island type conjugate fiber and the like, and the present invention is not limited only to those exemplified ones. Among them, the core-sheath type conjugate fiber is preferred from the viewpoint of efficient integration of a contact part between the constituent fibers, and the side-by-side type conjugate fiber is preferred when crimping is generated in the conjugate fiber by heating the conjugate fiber.

The conjugate fiber includes the resin A and the resin B. For example, the core-sheath type conjugate fiber and the side-by-side type conjugate fiber usually include two kinds of resins of the resin A and the resin B. The sea-island type conjugate fiber usually includes two to four kinds of resins containing the resin A and the resin B, preferably two or three kinds of resins containing the resin A and the resin B, more preferably the resin A and the resin B.

In the core-sheath type conjugate fiber, the resin B is used as a core component, and the resin A is used as a sheath component from the viewpoint of firm integration of a contact part between the constituent fibers with the resin A.

When the conjugate fiber is a core-sheath type conjugate fiber, it is preferred that the core component is not exposed to the surface of the conjugate fiber. In addition, it is preferred that the center of the core component in the direction of the fiber diameter is agreed with the center of the sheath component in the direction of the fiber diameter. In the core-sheath type conjugate fiber, a core-sheath structure can be formed in a concentric circle shape, or the core-sheath structure can be formed in an eccentric shape. The conjugate fiber having a core-sheath structure in which a core-sheath structure is formed in an eccentric shape is suitable for uses in which a crimp is required, since a crimp of the conjugate fiber is generated by heating the conjugate fiber. The cross-sectional shape of the core-sheath type conjugate fiber includes, for example, a circle, a triangle, a polygonal shape such as a quadrangle, an ellipse, an oval and the like, and the present invention is not limited only to those exemplified ones. Among these shapes, the circle is preferable. In addition, in the core-sheath type conjugate fiber, it is preferred that the volume ratio of the core component to the sheath component is from 30:70 to 70:30 from the viewpoint of improvement in strength of a single fiber and firm integration of a contact part of the constituent fibers with the resin A.

When the conjugate fiber is a core-sheath type conjugate fiber, the core-sheath type conjugate fiber can be produced by, for example, heating to melt the resin B and the resin A, which constitute the core component and the sheath component, respectively, introducing the molten resin B and the molten resin A into a conjugate spinning apparatus for producing a core-sheath type conjugate fiber, and extruding them from a core-sheath type conjugate nozzle to spin. Incidentally, when the resin A and the resin B are heated to melt, for example, a single screw extruder, a twin screw extruder, a kneader or the like can be used. As the core-sheath type conjugate nozzle, for example, a core-sheath type conjugate nozzle in which pores of the nozzle are arranged in a zigzag arrangement or an annular arrangement can be used.

Next, the spun core-sheath type conjugate fiber can be cooled to solidify by, for example, blowing cold air to the core-sheath type conjugate fiber.

The fineness of the conjugate fiber is preferably 0.5 to 15 denier, and more preferably 1 to 10 denier, from the viewpoint that a cosmetic which is incorporated into the elastic body for holding a cosmetic can be efficiently taken out to the outside, and that the elastic body for holding a cosmetic excellent in mechanical strength is obtained. Incidentally, the fineness of a fiber in the present invention means mass (g) of the fiber (filament) per 9000 m of its fiber length.

It is preferred that the fiber length of the conjugate fiber is 20 to 150 mm or so from the viewpoint that a cosmetic which is incorporated into the elastic body for holding a cosmetic can be efficiently taken out to the outside, and that the elastic body for holding a cosmetic excellent in mechanical strength is obtained.

The conjugate fiber can be subjected to processing such as antibacterial processing or antimicrobial processing as occasion demands from the viewpoint of imparting of antiseptic property to a cosmetic and the like which are used in a cosmetic product. In the processing, various methods can be employed, and the present invention is not limited by the methods.

The elastic body for holding a cosmetic of the present invention includes a conjugate fiber as a constituent fiber. The constituent fiber can be composed of only the conjugate fiber. Alternatively, the constituent fiber may contain the conjugate fiber and a fiber other than the conjugate fiber.

The fiber other than the conjugate fiber includes, for example, natural fibers such as cotton, linen and silk; regenerated fibers such as rayon; synthetic fibers; and the like. The present invention is not limited to only those exemplified ones. Among these fibers, the synthetic fiber is preferred from the viewpoint that a cosmetic which is incorporated into the elastic body for holding a cosmetic can be efficiently taken out to the outside, and that the elastic body for holding a cosmetic having an excellent mechanical strength is obtained.

The synthetic fiber includes, for example, polyester fibers such as a polyethylene terephthalate fiber, a polybutylene terephthalate fiber and a polytrimethylene terephthalate fiber, a polyvinyl chloride-based fiber, a polyvinylidene chloride fiber, a polypropylene fiber, a polyvinyl alcohol fiber, a polyamide fiber represented by a nylon 6 fiber, a polyimide fiber, a polyamideimide fiber, a cellulose acetate fiber and the like, and the present is not limited only to those exemplified ones. These fibers can be used alone, or at least two kinds thereof can be used in combination. Among these synthetic fibers, the polyester fiber and the polyamide fiber are preferable, and the polyester fiber is more preferable, from the viewpoint that a cosmetic which is incorporated into the elastic body for holding a cosmetic can be efficiently taken out to the outside, and that the elastic body for holding a cosmetic having an excellent light fastness is obtained.

The synthetic fiber can be subjected to processing such as antibacterial processing or antimicrobial processing as occasion demands from the viewpoint of imparting of antiseptic property to a cosmetic and the like which are used in a cosmetic product. In the processing, various kinds of methods can be employed, and the present invention is not limited by the kinds of the methods.

The melting temperature of the synthetic fiber is preferably higher than the melting temperature of the resin A by 20° C. or higher, and more preferably higher than the melting temperature of the resin A by 30° C. or higher, from the viewpoint of prevention of the synthetic fiber from permanent set in fatigue. The melting temperature of the synthetic fiber is preferably 150 to 270° C., and more preferably 160 to 270° C., from the viewpoint of prevention of the synthetic fiber from permanent set in fatigue, and efficient integration of the conjugated fiber and the synthetic fiber at the contact part of the conjugated fiber and the synthetic fiber.

The fineness of the synthetic fiber is preferably 0.5 to 15 denier, and more preferably 1 to 10 denier, from the viewpoint of obtaining of the elastic body for holding a cosmetic which can efficiently take out a cosmetic which is incorporated into the elastic body for holding a cosmetic to the outside.

It is preferred that the fiber length of the synthetic fiber is 20 to 150 mm or so from the viewpoint of obtaining of the elastic body for holding a cosmetic which can efficiently take out a cosmetic which is incorporated into the elastic body for holding a cosmetic to the outside, and which is excellent in mechanical strength.

It is preferred that the fiber length of the synthetic fiber is 20 to 150 mm or so from the viewpoint of obtaining of the elastic body for holding a cosmetic which can efficiently take out a cosmetic which is incorporated into the elastic body for holding a cosmetic to the outside, and which is excellent in mechanical strength.

In the present invention, it is preferred that the conjugate fiber and the synthetic fiber as a fiber other than the conjugate fiber are used in combination, more preferred that the conjugate fiber and the polyester fiber or the polyamide fiber are used in combination as the synthetic fiber, and furthermore preferred that the conjugate fiber and the polyester fiber are used in combination, from the viewpoint of obtaining of the elastic body for holding a cosmetic which can efficiently take out a cosmetic which is incorporated into the elastic body for holding a cosmetic to the outside, and which is excellent in light fastness.

The mass ratio of the conjugate fiber and the synthetic fiber (conjugate fiber/synthetic fiber) is preferably from 10/90 to 100/0, and more preferably from 30/70 to 80/20, from the viewpoint that the conjugate fiber is efficiently thermally fused with the synthetic fiber at the crossing part of the conjugate fiber and the synthetic fiber, and that the elastic body for holding a cosmetic, which can efficiently take out a cosmetic incorporated into the elastic body to the outside is obtained.

A method for producing a web sheet which is used for producing the elastic body for holding a cosmetic is described below with reference to drawings. The present invention is not limited only to the embodiment described in the drawings. In the following, although one embodiment in which the conjugate fiber and the synthetic fiber are used in combination is described, only the conjugate fiber can be used, or the conjugate fiber and a fiber other than the synthetic fiber can be used in combination.

FIG. 1 is a schematic explanatory drawing which shows one embodiment for producing a web sheet which is used in producing the elastic body for holding a cosmetic.

As shown in FIG. 1 (*a*), a web 1 is laminated. The web 1 can be formed by, for example, opening the conjugate fiber and the synthetic fiber, respectively, weighing each of them so that they have a predetermined ratio, and mixing them so as to have a uniform composition.

It is preferred that the thickness of the formed web is appropriately adjusted in accordance with the size of the elastic body for holding a cosmetic used.

Next, the web 1 is interposed between, for example, two flat plates (not shown in the figure). As occasion demands, the web 1 is pressed so as to have a predetermined thickness, and the web 1 is heated under this condition to a temperature which is equal to or higher than the melting temperature of the resin A which constitutes the conjugate fiber included in the web 1, and which is lower than the melting temperature of the resin B which constitutes the conjugate fiber and the melting temperature of the synthetic fiber, to melt the resin A. Thereby, the contact part of the constituent fibers containing the conjugate fiber, and the synthetic fiber is fused to form into one body by the resin A, and a web 2 can be obtained as shown in FIG. 1 (*b*). At that time, as occasion demands, a lump (ameba-like) fusion part made of the resin A can be formed at the crossing part of the constituent fibers by putting the web sheet 2 in a molding die so that the web sheet 2 has a predetermined density, heating the web sheet 2 in the same manner as in the case mentioned above, to melt the resin A and bond the constituent fibers at the crossing part with the molten resin A. In FIG. 1 (*b*), the above-mentioned fusion part is indicated by a symbol A.

In the web sheet 2 thus obtained, the constituent fibers are bonded with each other at their crossing parts in a point-like shape by the molten resin A, and the bonded fibers are aligned in the plane direction of the web sheet 2.

Next, the web sheet 2 obtained in the above is cut in a vertical direction as indicated by an arrow B shown in FIG. 1 (*c*). As shown in FIG. 1 (*d*), a cut web sheet 3 is arranged so that the cut face is a top face or a lower face. In the web sheet 3, a structure like a jungle gym (a three-dimensional structure) is formed in the thickness direction. Accordingly, it is considered that the web sheet 3 is excellent in cushioning property since the web sheet 3 shows a high repulsion to a pressure from the upper surface of the web sheet 3, and also excellent in resistance to "permanent set in fatigue".

Incidentally, when the conjugate fiber and the synthetic fiber are arranged so as to be parallel to the length direction of the fibers at the time of mixing the conjugate fiber with the synthetic fiber, and piled up, to give the web sheet 3, a stripe showing that both of the conjugate fiber and the synthetic fiber are parallel to each other appears at the time of elongating the web sheet 3 in the direction of an Arrow C shown in FIG. 1 (d). The stripe becomes an index showing that the web sheet 3 is produced by the above-mentioned method.

Next, the web sheet 3 obtained in the above can be cut so as to have a desired size and a desired shape, to obtain the elastic body for holding a cosmetic.

The size and shape of the elastic body for holding a cosmetic cannot be absolutely determined because the size and shape differ depending on uses of the elastic body for holding a cosmetic. Accordingly, it is preferred that the size and shape of the elastic body for holding a cosmetic are appropriately adjusted in accordance with the uses of the elastic body for holding a cosmetic.

As one embodiment of the elastic body for holding a cosmetic, there can be cited, for example, an elastic body for holding a cosmetic having a circular plane shape of a diameter of 3 to 15 cm or so, and a cylindrical shape having a thickness of 0.5 to 5 cm or so, and the like. The elastic body for holding a cosmetic can be suitably used, for example, as an elastic body for holding a liquid cosmetic such as a foundation.

The density of the elastic body for holding a cosmetic of the present invention cannot be absolutely determined because the density differs depending on uses of the elastic body for holding a cosmetic, and the like. The density is usually preferably from 6 to 50 $kg/m^3$ or so, and more preferably from 6 to 30 $kg/m^3$ or so.

The Asker F hardness of the elastic body for holding a cosmetic of the present invention cannot be absolutely determined because the Asker F hardness differs depending on uses of the elastic body for holding a cosmetic, and the like. The Asker F hardness is usually preferably from 30 to 60 or so. Incidentally, the Asker F hardness of the elastic body for holding a cosmetic described herein is a value as determined at a temperature of 25° C. by using an Asker rubber hardness meter of type F, which is manufactured by KOBUNSHI KEIKI CO., LTD.

Incidentally, it is preferred that both of the conjugated fiber and the synthetic fiber which are bonded at their crossing points are arranged in the thickness direction of the web sheet 3 as shown in FIG. 1 (d) from the viewpoint of prevention of the elastic body for holding a cosmetic of the present invention from permanent set in fatigue at the time of use.

The scale of permanent set in fatigue of the elastic body for holding a cosmetic when the elastic body is continuously used (hereinafter referred to as "degree of permanent set in fatigue") is preferably 20% or less, and more preferably 10% or less, from the viewpoint of prevention of permanent set in fatigue at the time of use. Incidentally, the degree of permanent set in fatigue of the elastic body for holding a cosmetic as described herein is a value as determined by the following equation:

[Degree of permanent set in fatigue of an elastic body for holding a cosmetic (%)]={[Permanent set in fatigue of the elastic body for holding a cosmetic (mm)]÷[Initial thickness of the elastic body for holding a cosmetic (mm)]}×100·n In addition, the permanent set in fatigue of the elastic body for holding a cosmetic (mm) is a value as determined by a method described in the following working examples.

In the elastic body for holding a cosmetic of the present invention obtained in the above, the conjugate fiber contains the resin A and the resin B of which melting temperature is higher than that of the resin A, and the contact part of the constituent fibers is united into one body by the resin A of the conjugate fiber, so that gaps are existed between the constituent fibers, and the gaps are fixed. Accordingly, since a cosmetic which is incorporated into the elastic body for holding a cosmetic can be efficiently taken out from the gaps between the constituent fibers to the outside, the remaining ratio of the cosmetic in the elastic body after use can be reduced.

In addition, since the elastic body for holding a cosmetic of the present invention has a three-dimensional structure, the amount of the cosmetic being incorporated into the elastic body, which is taken out from the elastic body can be suppressed from the initial stage of use.

In addition, the elastic body for holding a cosmetic of the present invention is excellent in light fastness, and has an advantageous merit such that yellowing caused by sunlight or the like can be suppressed. The light fastness is effectively exhibited when the resin A is the polyester or the polyester elastomer, and the resin B is the thermoplastic polyester in the conjugate fiber, and the other fiber is a polyester single fiber (filament) in case that the other fiber is included in the constituent fibers.

In addition, the elastic body for holding a cosmetic of the present invention is also excellent in holding property (non-adsorbing property) of an ultraviolet absorbent contained in a cosmetic, and moreover excellent in durability because permanent set in fatigue of an elastic body is small after repeated use.

Accordingly, the elastic body for holding a cosmetic of the present invention can be suitably used as a cosmetic-containing elastic body by holding a cosmetic in the elastic body, and the cosmetic-containing elastic body can be suitably used in various cosmetic products.

The cosmetic-containing elastic body of the present invention exhibits effects based on the elastic body for holding a cosmetic, because the elastic body for holding a cosmetic is used in the cosmetic-containing elastic body. In addition, the cosmetic product of the present invention exhibit effects based on the cosmetic-containing elastic body, because the cosmetic-containing elastic body is used in the cosmetic product.

The cosmetic which can be used in the cosmetic-containing elastic body of the present invention include, for example, foundation, makeup base, eye shadow, eye liner, mascara, blusher, face powder, eyebrow pencil, cleansing cream, cleansing milk, cleansing liquid, facial cleansing cream, facial cleansing foam, massage cream, cold cream, vanishing cream, skin cream, skin gel, emulsion, face lotion, essence, various lotions, sunscreen, body cream, body oil, hair shampoo, hair rinse, hair conditioner, hair treatment, hair liquid, hair tonic and the like, and the present invention is not limited only to those exemplified ones. Among these cosmetics, a liquid cosmetic is preferable, since the cosmetic-containing elastic body of the present invention exhibits excellent effects for the liquid cosmetic.

The viscosity of the cosmetic is not particularly limited. The viscosity of the cosmetic at 25° C. is preferably from 500 to 50000 mPa·s, more preferably from 500 to 30000 mPa·s, further preferably from 1000 to 20000 mPa·s, and even more preferably from 1000 to 10000 mPa·s in the present invention. Incidentally, the viscosity of the cosmetic is a value as determined by using a BM type viscometer.

The amount of the cosmetic which is used in the cosmetic-containing elastic body of the present invention cannot be absolutely determined because the amount differs depending on the kind of a cosmetic product. For example, when the cosmetic product is a liquid foundation, the liquid foundation having a viscosity of 6000 mPa·s at 25° C. can be used in an amount of 10 to 20 g or so in the cosmetic-containing elastic body having a diameter of 5 cm and a thickness of 1.5 cm.

A pad for holding a cosmetic includes the elastic body for holding a cosmetic according to the present invention. Since the pad for holding a cosmetic includes the above-mentioned elastic body for holding a cosmetic, the pad for holding a cosmetic exhibits effects based on the above-mentioned elastic body for holding a cosmetic.

The pad for holding a cosmetic may contain only the elastic body for holding a cosmetic of the present invention. Alternatively, the pad for holding a cosmetic may contain components such as an elastic body other than the above-mentioned elastic body for holding a cosmetic, a fiber, a resin and a film within a scope which would not hinder an object of the present invention.

The pad for holding a cosmetic may have a laminated structure. When the pad for holding a cosmetic has a laminated structure, it is preferred that at least the surface layer of the layers of the pad for holding a cosmetic in a plane direction is the elastic body for holding a cosmetic of the present invention from the viewpoint of obtaining a pad for holding a cosmetic capable of efficiently taking out a cosmetic which is incorporated into the pad for holding a cosmetic to the outside.

The pad for holding a cosmetic can be used after the pad for holding a cosmetic is cut so as to have a desired size and a desired shape as occasion demands. The size and shape of the pad for holding a cosmetic cannot be absolutely determined, because the size and shape differ depending on uses of the pad for holding a cosmetic. Accordingly, it is preferred that the size and shape of the pad for holding a cosmetic are appropriately adjusted in accordance with the uses of the pad for holding a cosmetic.

As one embodiment of the pad for holding a cosmetic, there can be cited, for example, a pad for holding a cosmetic having a circular plane shape of a diameter of from 3 to 15 cm or so, and a cylindrical shape having a thickness of from 0.5 to 5 cm or so, and the like. The pad for holding a cosmetic can be suitably used, for example, as a pad for holding a cosmetic for holding a liquid cosmetic such as a foundation.

The density of the pad for holding a cosmetic cannot be absolutely determined because the density differs depending on uses of the pad for holding a cosmetic, and the like. The density of the pad is usually preferably from 6 to 50 kg/m$^3$ or so, and more preferably from 6 to 30 kg/m$^3$ or so.

The Asker F hardness of the pad for holding a cosmetic cannot be absolutely determined because the Asker F hardness differs depending on uses of the pad for holding a cosmetic, and the like. The Asker F hardness is usually preferably from 30 to 60 or so. Incidentally, the Asker F hardness of the pad for holding a cosmetic is a value as determined in the same manner as in determining the Asker F of the above-mentioned elastic body for holding a cosmetic material.

The degree of permanent set in fatigue of the pad for holding a cosmetic is preferably 20% or less, and more preferably 10% or less, from the viewpoint of prevention of permanent set in fatigue at the time of use. Incidentally, the degree of permanent set in fatigue of the pad for holding a cosmetic is a value as determined in the same manner as in determining the degree of permanent set in fatigue of the above-mentioned elastic body for holding a cosmetic material.

The pad for holding a cosmetic can be suitably used as a cosmetic-containing pad by including a cosmetic in the pad for holding a cosmetic, and the cosmetic-containing pad can be suitably used in various cosmetic products.

Since the above-mentioned pad for holding a cosmetic is used in the cosmetic-containing pad, the cosmetic-containing pad exhibits effects based on the pad for holding a cosmetic. In addition, since the above-mentioned cosmetic-containing pad is used in the above-mentioned cosmetic product, the cosmetic product exhibits effects based on the cosmetic-containing pad.

As the cosmetic which can be used in the cosmetic-containing pad, there can be exemplified the same cosmetic as used in the above-mentioned cosmetic-containing elastic body. In addition, as the viscosity and amount of the cosmetic which is used in the cosmetic-containing pad, there can be exemplified the same viscosity and amount of the cosmetic as mentioned above.

EXAMPLES

Next, the present invention is more specifically described based on working examples. However, the present invention is not limited only to the working examples.

Example 1

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 40:60 so as to arrange each fiber in parallel with each other, to give a web, and the web was heated to melt the sheath component in a pressing state, to give an elastic body for holding a cosmetic. The elastic body for holding a cosmetic was processed by cutting to give a sample A having a diameter of 5 cm and a thickness of 1.4 cm (density: 13.4 kg/m$^3$).

When the sample A obtained in the above was stretched in the direction of the arrow C shown in FIG. 1 (*d*), a stripe derived from the lamination of the web 1 in producing was observed. However, when the sample A was stretched in the direction perpendicular to the direction of the arrow C, a stripe was not observed.

Figure 2:
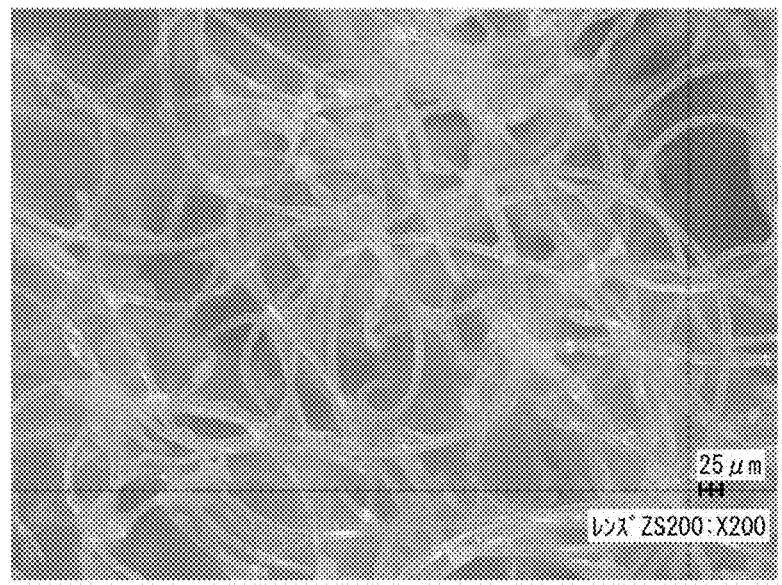
FIG. 2 (a) is an optical microscope photograph substituted with a drawing, which shows a cross section of a sample A obtained in Example 1 in a plane direction.
Figure 2:
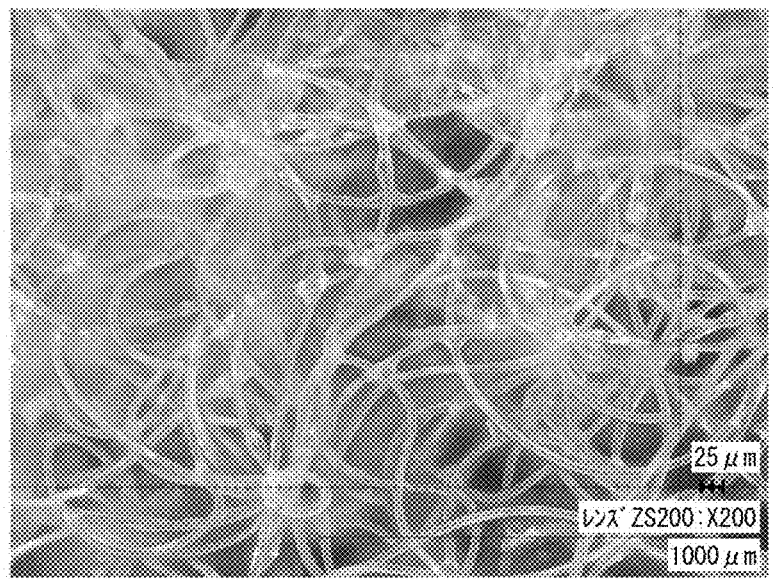

Next, the plane surface and the side surface of the sample A obtained in the above were observed with an optical microscope. Their results are shown in FIG. 2. In FIG. 2, (a) shows an optical microscope photograph of the sample A in a cross section of a plane direction, and (b) shows a microscope photograph of the sample A in a cross section of a thickness direction. Incidentally, the magnification of each photograph is shown at the lower part of each photograph, and the length per scale is 25 μm.

From the results shown in FIG. 2, it can be seen that the fiber density of the side face of the sample A is higher than that of the plane surface of the sample A, and that a lump (ameba-like) fusion part is formed at the contacting part of the constituent fibers.

Example 2

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 70:30 so as to arrange each fiber in parallel with each other, to give a web, and the web was heated to melt the sheath component in a pressing state, to give an elastic body for holding a cosmetic. The elastic body for holding a cosmetic was processed by cutting to give a sample B having a diameter of 5 cm and a thickness of 1.5 cm (density: 12.9 kg/m$^3$).

When the sample B obtained in the above was stretched in the direction of the arrow C shown in FIG. 1 (d), a stripe derived from the lamination of the web 1 in producing was observed. However, when the sample B was stretched in the direction perpendicular to the direction of the arrow C, a stripe was not observed. In addition, it was confirmed that a lump (ameba-like) fusion part was formed at the contacting part of the constituent fibers, as well as Example 1.

Example 3

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 50:50 so as to arrange each fiber in parallel with each other, to give a web, and the web was heated to melt the sheath component in a pressing state, to give an elastic body for holding a cosmetic. The elastic body for holding a cosmetic was processed by cutting to give a sample C having a diameter of 5 cm and a thickness of 1.6 cm (density: 17.1 kg/m$^3$).

When the sample C obtained in the above was stretched in the direction of the arrow C shown in FIG. 1 (d), a stripe derived from the lamination of the web 1 in producing was observed. However, when the sample C was stretched in the direction perpendicular to the direction of the arrow C, a stripe was not observed. In addition, it was confirmed that a lump (ameba-like) fusion part was formed at the contacting part of the constituent fibers, as well as Example 1.

Example 4

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 70:30 so as to arrange each fiber in parallel with each other, to give a web, and the web was heated to melt the sheath component in a pressing state, to give an elastic body for holding a cosmetic. The elastic body for holding a cosmetic was processed by cutting to give a sample D having a diameter of 5 cm and a thickness of 1.5 cm (density: 14.0 kg/m$^3$).

When the sample D obtained in the above was stretched in the direction of the arrow C shown in FIG. 1 (d), a stripe derived from the lamination of the web 1 in producing was observed. However, when the sample D was stretched in the direction perpendicular to the direction of the arrow C, a stripe was not observed. In addition, it was confirmed that a lump (ameba-like) fusion part was formed at the contacting part of the constituent fibers, as well as Example 1.

Example 5

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 40:60 so as to arrange each fiber in parallel with each other, to give a web, and the web was heated to melt the sheath component in a pressing state, to give an elastic body for holding a cosmetic. The elastic body for holding a cosmetic was processed by cutting to give a sample E having a diameter of 5 cm and a thickness of 1.6 cm (density: 14.2 kg/m$^3$).

When the sample E obtained in the above was stretched in the direction of the arrow C shown in FIG. 1 (d), a stripe derived from the lamination of the web 1 in producing was observed. However, when the sample E was stretched in the direction perpendicular to the direction of the arrow C, a stripe was not observed. In addition, it was confirmed that a lump (ameba-like) fusion part was formed at the contacting part of the constituent fibers, as well as Example 1.

Example 6

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 50:50 so as to arrange each fiber in parallel with each other, to give a web, and the web was heated to melt the sheath component in a pressing state, to give an elastic body for holding a cosmetic. The elastic body for holding a cosmetic was processed by cutting to give a sample F having a diameter of 6 cm and a thickness of 1.1 cm (density: 16.4 kg/m$^3$).

When the sample F obtained in the above was stretched in the direction of the arrow C shown in FIG. 1 (d), a stripe derived from the lamination of the web 1 in producing was observed. However, when the sample F was stretched in the direction perpendicular to the direction of the arrow C, a stripe was not observed. In addition, it was confirmed that a lump (ameba-like) fusion part was formed at the contacting part of the constituent fibers, as well as Example 1.

Example 7

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 70:30 so as to arrange each fiber in parallel with each other, to give a web, and the web was heated to melt the sheath component in a pressing state, to give an elastic body for holding a cosmetic. The elastic body for holding a cosmetic was processed by cutting to give a sample G having a diameter of 6 cm and a thickness of 1.5 cm (density: 17.1 kg/m$^3$).

When the sample G obtained in the above was stretched in the direction of the arrow C shown in FIG. 1 (d), a stripe derived from the lamination of the web 1 in producing was observed. However, when the sample G was stretched in the direction perpendicular to the direction of the arrow C, a stripe was not observed. In addition, it was confirmed that a lump (ameba-like) fusion part was formed at the contacting part of the constituent fibers, as well as Example 1.

Example 8

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 20:80 so as to arrange each fiber in parallel with each other, to give a web, and the web was heated to melt the sheath component in a pressing state, to give an elastic body for holding a cosmetic. The elastic body for holding a cosmetic was processed by cutting to give a sample H having a diameter of 5 cm and a thickness of 1.4 cm (density: 18.9 kg/m$^3$). Incidentally, the Asker F hardness of the sample H was 39.

When the sample H obtained in the above was stretched in the direction of the arrow C shown in FIG. 1 (*d*), a stripe derived from the lamination of the web 1 in producing was observed. However, when the sample H was stretched in the direction perpendicular to the direction of the arrow C, a stripe was not observed. In addition, it was confirmed that a lump (ameba-like) fusion part was formed at the contacting part of the constituent fibers, as well as Example 1.

Example 9

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 40:60 so as to arrange each fiber in parallel with each other, to give a web, and the web was heated to melt the sheath component in a pressing state, to give an elastic body for holding a cosmetic. The elastic body for holding a cosmetic was processed by cutting to give a sample I having a diameter of 5 cm and a thickness of 1.4 cm (density: 20.5 kg/m$^3$). Incidentally, the Asker F hardness of the sample I was 51.4.

When the sample I obtained in the above was stretched in the direction of the arrow C shown in FIG. 1 (*d*), a stripe derived from the lamination of the web 1 in producing was observed. However, when the sample I was stretched in the direction perpendicular to the direction of the arrow C, a stripe was not observed. In addition, it was confirmed that a lump (ameba-like) fusion part was formed at the contacting part of the constituent fibers, as well as Example 1.

Example 10

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 50:50 so as to arrange each fiber in parallel with each other, to give a web, and the web was heated to melt the sheath component in a pressing state, to give an elastic body for holding a cosmetic. The elastic body for holding a cosmetic was processed by cutting to give a sample J having a diameter of 5 cm and a thickness of 1.4 cm (density: 19.9 kg/m$^3$). Incidentally, the Asker F hardness of the sample J was 54.2.

When the sample J obtained in the above was stretched in the direction of the arrow C shown in FIG. 1 (*d*), a stripe derived from the lamination of the web 1 in producing was observed. However, when the sample J was stretched in the direction perpendicular to the direction of the arrow C, a stripe was not observed. In addition, it was confirmed that a lump (ameba-like) fusion part was formed at the contacting part of the constituent fibers, as well as Example 1.

Example 11

A core-sheath type conjugate fiber [core component: polyethylene terephthalate, sheath component: thermoplastic polyethylene terephthalate, fineness: 6 denier] was mixed with a polyester fiber (resin: polyethylene terephthalate, fineness: 3 denier) in a mass ratio of 70:30 so as to arrange each fiber in parallel with each other, to give a web, and the web was heated to melt the sheath component in a pressing state, to give an elastic body for holding a cosmetic. The elastic body for holding a cosmetic was processed by cutting to give a sample K having a diameter of 5 cm and a thickness of 1.4 cm (density: 18.9 kg/m$^3$). Incidentally, the Asker F hardness of the sample K was 51.4.

When the sample K obtained in the above was stretched in the direction of the arrow C shown in FIG. 1 (*d*), a stripe derived from the lamination of the web 1 in producing was observed. However, when the sample K was stretched in the direction perpendicular to the direction of the arrow C, a stripe was not observed. In addition, it was confirmed that a lump (ameba-like) fusion part was formed at the contacting part of the constituent fibers, as well as Example 1.

Example 12

A web composed only of a core-sheath type conjugate fiber [core component: polyethylene terephthalate, sheath component: thermoplastic polyethylene terephthalate, fineness: 6 denier] was heated to melt the sheath component in a pressing state, to give an elastic body for holding a cosmetic. The elastic body for holding a cosmetic was processed by cutting to give a sample L having a diameter of 5 cm and a thickness of 1.4 cm (density: 15.4 kg/m$^3$). Incidentally, the Asker F hardness of the sample L was 43.2.

When the sample L obtained in the above was stretched in the direction of the arrow C shown in FIG. 1 (*d*), a stripe derived from the lamination of the web 1 in producing was observed. However, when the sample L was stretched in the direction perpendicular to the direction of the arrow C, a stripe was not observed. In addition, it was confirmed that a lump (ameba-like) fusion part was formed at the contacting part of the constituent fibers, as well as Example 1.

Comparative Example 1

A sample R1 made of a polyether polyurethane foam, having a diameter of 5 cm and a thickness of 1.5 cm was prepared.

Comparative Example 2

A sample R2 made of a nitrile rubber foam, having a diameter of 5 cm and a thickness of 1.5 cm was prepared.

Experimental Example 1

The light fastness test of the sample A, the sample B, the sample C, the sample R1 and the sample R2 were carried out on the basis of the following conditions:
[Conditions for Light Fastness Test]
Testing instrument: manufactured by Suga Test Instruments Co., Ltd., Product name: Ultraviolet auto-fade meter U48AU Test method: using the above-mentioned test instrument, each sample was irradiated with ultraviolet rays for 7 hours, and the surface state of the sample before and after the irradiation of the ultraviolet rays was examined.

Figure 3:
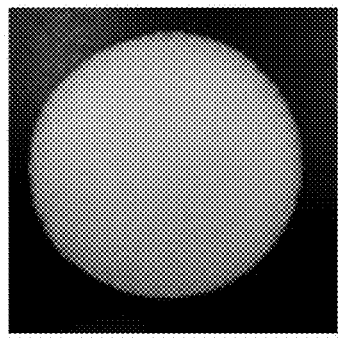
FIG. 3 (a) is an optical microscope photograph substituted with a drawing, which shows a result of a light fastness test of the sample A in Experimental example 1.
Figure 3:
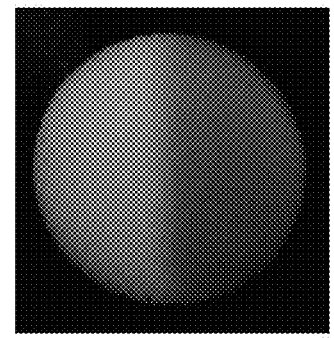
Figure 3:
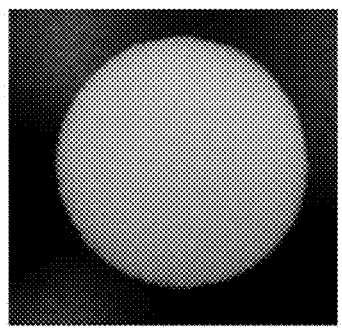
Figure 3:
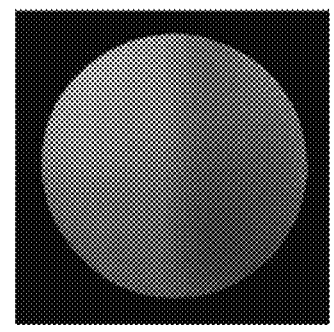
Figure 3:
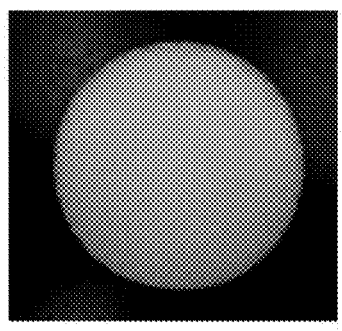

The results of light fastness test of each sample were sequentially shown in FIG. 3 (*a*) to (*e*). In each figure, the left half of the figure facing the paper surface is the surface state of the sample before irradiation of ultraviolet rays, and the right half of the figure facing the paper surface is the surface state of the sample after irradiation of ultraviolet rays.

From the results shown in FIG. 3, as to the samples A to C, no change in surface state was observed as shown in FIG. 3 (*a*) to (*c*), respectively. To the contrary, in the sample R1, remarkable yellowing (deep color part of the right half of the figure facing the paper surface) due to the irradiation of ultraviolet rays was observed as shown in FIG. 3 (d), and in the sample R2, a little yellowing (dark color part of the right half of the figure facing the paper surface) due to the irradiation of ultraviolet rays was observed as shown in the FIG. 3 (e).

Accordingly, according to each Example, it can be seen that an elastic body for holding a cosmetic, which is excellent in light fastness is obtained as shown by the samples A to C.

Experimental Example 2

A dumbbell specimen (length of test part: 30 mm, width of test part: 10 mm, thickness of test part: 15 mm) was cut out from each sample of the samples A to E and the samples G to L. The specimen was attached to a tensile test machine [manufactured by Shimadzu Corporation under the product name of Autograph AGS-100G] so that the chuck distance of the tensile test machine was 30 mm, and a tensile test was carried out at a tensile speed of 100 mm/min. The results are shown in Table 1.

Incidentally, the specimen having a stripe based on fibers, which was parallel to the tensile direction of the specimen was used as a vertical type specimen, and the specimen having a stripe based on fibers, which was vertical to the tensile direction of the specimen was used as a horizontal type specimen. These two kinds of the specimens were used when the tensile test was carried out.

TABLE 1

| | Tensile strength (N) | |
|---|---|---|
| Kind of sample | Vertical type specimen | Horizontal type specimen |
| Sample A | 4.13 | 1.03 |
| Sample B | 10.02 | 2.48 |
| Sample C | 11.36 | 2.60 |
| Sample D | 11.88 | 3.16 |
| Sample E | 5.02 | 0.75 |
| Sample G | 18.84 | 3.60 |
| Sample H | 5.97 | 0.69 |
| Sample I | 16.49 | 2.14 |
| Sample J | 22.56 | 3.04 |
| Sample K | 22.26 | 3.74 |
| Sample L | 26.29 | 6.54 |

From the results shown in Table 1, since the sample obtained in each Example has a favorable tensile strength, and the tensile strength can be widely adjusted, it can be seen that the tensile strength of an elastic body for holding a cosmetic can be appropriately adjusted in accordance with the kind of the cosmetic product. In addition, it can be seen that the specimen having a stripe based on fibers, which is parallel to the tensile direction of the specimen is more excellent in tensile strength than the specimen having a stripe based on fibers, which is vertical to the tensile direction of the specimen.

Experimental Example 3

The sample E, the sample F, the sample G, the sample R1 and the sample R2 were used, and the initial mass of each sample was weighed.

The plane surface of each sample was uniformly coated with a mineral water-based foundation [manufactured by Shiseido Company, Limited, viscosity: 2000 mPa·s] in an amount of 15 g. Thereafter, the sample was allowed to stand for one hour, to impregnate the foundation into the sample.

Next, a procedure for lightly pressing the surface of each sample with a cosmetic puff by a panelist, and then wiping the foundation attached to the cosmetic puff was regarded as one cycle. The procedure was repeatedly carried out until the foundation was hardly attached to the cosmetic puff, and the cycle of the procedure was counted. The number of the cycle was used as an index of persistence of the cosmetic. In addition, when the foundation was hardly attached to the cosmetic puff, each sample was weighed as a final mass of the sample.

The residual rate of a cosmetic (foundation) was determined by using the initial mass of each sample and the final mass of each sample in accordance with the equation:

[Residual rate of a cosmetic]={[(Initial mass of a sample)−(Final mass of a sample)]÷[Amount of a cosmetic used (15 g)]}×100.

The above results are shown in Table 2.

TABLE 2

| Kind of sample | Persistence of cosmetic [cycle(s)] | Residual rate of cosmetic (%) |
|---|---|---|
| Sample E | 173 | 12.7 |
| Sample F | 174 | 10.9 |
| Sample G | 207 | 13.4 |
| Sample R1 | 164 | 20.0 |
| Sample R2 | 150 | 33.9 |

From the results shown in Table 2, it can be seen that the samples E to G are more excellent in persistence of a cosmetic than the conventional samples R1 and R2, and that according to the samples E to G, a cosmetic can be efficiently used up to the final use because the residual rate of the cosmetic is remarkably low after the use of the sample.

In addition, as to the samples H, J and K, persistence (cycle) of a cosmetic was carried out in the same manner as in Experimental example 3. As a result, each persistence (cycle) of a cosmetic of the samples H, J and K was 180 times, 192 times and 178 times, respectively. From these results and the results shown in Table 2, it can be seen that the samples H, J and K are more excellent in persistence of a cosmetic than the conventional samples R1 and R2.

Experimental Example 4

A test solution was prepared by mixing 900 g of liquid paraffin with 100 g of an ultraviolet absorbing agent (2-ethylhexyl p-methoxycinnamate).

A blank sample produced by putting the test solution in a petri dish, the sample A with which 30 g of the test liquid was impregnated, the sample R1 with which 30 g of the test liquid was impregnated, and the sample R2 with which 30 g of the test liquid was impregnated were prepared. Each sample was placed in a thermos-hygrostat having a temperature of 25° C. and a relative humidity of 60%, and each sample was allowed to stand for 4 days. Thereafter, the amount of the ultraviolet absorbing agent included in the test solution of the blank sample and each sample was quantified by means of a liquid chromatography under the following measurement conditions. Incidentally, the amount of the ultraviolet absorbing agent was determined based on a previously prepared calibration curve.

[Measurement Conditions of Liquid Chromatography]

Measuring device: manufactured by Waters Corporation under the product name of ACQUITY UPLCH-Class Detector: manufactured by Waters Corporation under the product name of TUV (detection wavelength: 310 nm)

Column: manufactured by Waters Corporation under the product name of ACQUITY UPLC-BEH C-8 (inner diameter: 2.1 mm, length: 10 cm)

Measurement temperature: 50° C.

Mobile phase: mixed solvent of 50% by mass of water and 50% by mass of acetonitrile Flow rate: 0.5 ml/min

TABLE 3

| Kind of sample | Residual content of ultraviolet absorbing agent |
| --- | --- |
| Sample A | 99.0 |
| Sample R1 | 97.0 |
| Sample R2 | 84.0 |

From the results shown in Table 3, since the residual content of the ultraviolet absorbing agent in the sample A obtained in the working example of the present invention is higher than that in the conventional sample R1 and sample R2, it can be seen that the sample A is excellent in holding property of an ultraviolet absorbing agent over a long period of time.

From the above results, since the elastic body for holding a cosmetic of the present invention is excellent in retention property of an ultraviolet absorbing agent, it can be seen that the elastic body for holding a cosmetic of the present invention can be suitably used for, for example, a cosmetic product such as a foundation.

Experimental Example 5

A mineral water-based foundation (manufactured by Shiseido Company, Limited) was uniformly applied to the samples A to G and the sample R1 in an amount of 15 g, and allowed to stand for one hour, to impregnate the foundation into each sample.

Next, a procedure for lightly pressing the surface of each sample with a cosmetic puff by a panelist, and then wiping the foundation attached to the cosmetic puff twice per one day was regarded as one cycle. The procedure was repeatedly carried out for 30 days. As a result, it was confirmed that permanent set in fatigue of the samples A to G was comparable to that of the sample R1. In addition, each surface of the samples A to G was visually observed after the repeat of the cycle for 30 days. As a result, no fluffing was observed on the surface of each sample.

Experimental Example 6

After persistence of a cosmetic of the sample K was evaluated in Experimental example 3, the final thickness of the sample K was measured. On the basis of the initial thickness (1.4 cm) of the sample K and the above-mentioned final thickness of the sample K, permanent set in fatigue (mm) of the sample K was determined in accordance with the equation:

[Permanent set in fatigue (mm) of the sample $K$]= [Initial thickness of the sample $K$ (mm)]−[Final thickness (mm) of the sample $K$].

As a result, the permanent set in fatigue was found to be 1.1 mm.

On the basis of the permanent set in fatigue (mm) of the sample K as determined above, the degree of permanent set in fatigue of the sample K was determined. As a result, the degree of permanent set in fatigue of the sample K was found to be 7.8%. It can be seen from this result that the sample K has a low permanent set in fatigue due to continuous use.

From the above results, since the elastic body for holding a cosmetic of the present invention is small in permanent set in fatigue due to continuous use, and moreover the elastic body maintains an appropriate surface condition without fluffing even when the surface of the elastic body is repeatedly rubbed by a cosmetic puff, it can be seen that the elastic body can be suitably used in, for example, a cosmetic product such as a foundation.

DESCRIPTION OF SYMBOLS

1: Web
2: Web sheet
3: Cut web sheet

The invention claimed is:

1. An elastic body for holding a cosmetic, comprising constituent fibers containing a conjugate fiber, wherein the conjugate fiber comprises a resin A that contains a polyester or a polyester elastomer, and a resin B that contains a thermoplastic polyester and has a melting temperature higher than a melting temperature of the resin A, and wherein a contact part between the constituent fibers is integrated with the resin A.

2. A cosmetic-containing elastic body comprising a cosmetic and the elastic body for holding a cosmetic according to claim 1, wherein the cosmetic is included in the elastic body for holding a cosmetic.

3. A cosmetic product comprising the cosmetic-containing elastic body according to claim 2.

4. The elastic body for holding a cosmetic according to claim 1, wherein the constituent fibers further comprise a synthetic fiber other than the conjugate fiber, the synthetic fiber containing a polyester fiber or a polyamide fiber.

5. The elastic body for holding a cosmetic according to claim 4, wherein a mass ratio of the conjugate fiber and the synthetic fiber (conjugate fiber/synthetic fiber) is from 10/90 to 100/0.

6. The elastic body for holding a cosmetic according to claim 4, wherein a mass ratio of the conjugate fiber and the synthetic fiber (conjugate fiber/synthetic fiber) is from 10/90 to 80/20.

7. The elastic body for holding a cosmetic according to claim 4, wherein a mass ratio of the conjugate fiber and the synthetic fiber (conjugate fiber/synthetic fiber) is from 30/70 to 80/20.

8. The elastic body for holding a cosmetic according to claim 4, wherein the elastic body comprises a web sheet comprising the conjugate fiber and the synthetic fiber, wherein the conjugate fiber and the synthetic fiber are arranged in a thickness direction of the web sheet.

* * * * *